United States Patent [19]
Ohsaki et al.

[11] Patent Number: 6,088,115
[45] Date of Patent: Jul. 11, 2000

[54] APPARATUS AND METHOD FOR MEASURING OPTICAL ANISOTROPY

[75] Inventors: Yoshinori Ohsaki, Utsunomiya; Takashi Suzuki, Yokohama, both of Japan

[73] Assignee: Canon Kabushiki Kaisha, Tokyo, Japan

[21] Appl. No.: 08/866,216

[22] Filed: May 30, 1997

[30] Foreign Application Priority Data

Jun. 5, 1996 [JP] Japan ..................................... 8-143304

[51] Int. Cl.[7] .................................................. G01N 21/55
[52] U.S. Cl. ........................................... 356/445; 356/369
[58] Field of Search ..................................... 356/445, 369

[56] References Cited

U.S. PATENT DOCUMENTS

| | | | |
|---|---|---|---|
| 4,181,441 | 1/1980 | Noller | 356/414 |
| 5,394,245 | 2/1995 | Sato | 356/369 |

FOREIGN PATENT DOCUMENTS

| | | |
|---|---|---|
| 0 575 132 | 12/1993 | European Pat. Off. . |
| 0 724 147 | 7/1996 | European Pat. Off. . |
| 42 11 467 | 10/1993 | Germany . |
| 6-34530 | 2/1994 | Japan . |
| 989403 | 1/1983 | U.S.S.R. . |

OTHER PUBLICATIONS

Xue, J., et al., "Surface Orientation Transitions in Surface Stabilized Ferroelectric Liquid Crystal Structures", Appl. Phys. Lett. 53 (24), pp. 2397–2399 (Dec. 1988).

Hinov, H.P., et al., "Total Internal Reflection from Nematic Liquid Crystals", Revue Phys. Appl. 15, pp. 1307–1321 (Aug. 1980).

Takezoe, H., et al., "Experimental Studies on Reflection Spectra in Monodomain Cholesteric Liquid Crystal Calls: Total Reflection, Subsidiary Oscillation and Its Beat or Swell Structure," Japanese Journal of Applied Physics, vol. 22, No. 7, pp. 1080–1091 (Jul. 1983).

Yamashita, M., "Dependence of Temporal Behavior of Conoscopic Figures in Nematic Liquid Crystals on Film Thickness," Japanese Journal of Applied Physics, vol. 25, No. 1, pp. 1–7 (Jan. 1986).

*Primary Examiner*—Frank G. Font
*Assistant Examiner*—Tu T. Nguyen
*Attorney, Agent, or Firm*—Fitzpatrick, Cella, Harper & Scinto

[57] ABSTRACT

In an optical anisotropy measurement apparatus for emitting a light flux from a He-Ne laser to be incident to an object to be examined, such as a liquid crystal in a liquid crystal cell, and detecting a light flux totally reflected from the object to be examined to measure an optical anisotropy of the object, a portion of the incident light flux is designed to be incident at an angle smaller than a critical angle of total reflection to and transmitted through the object to be examined. As a result, a light flux-incident region causing total reflection at the boundary is allowed to have a shape closer to a circle and have a smaller size, thus allowing detection of a local alignment change in optical anisotropy as caused by, e.g., a minute alignment defect in a liquid crystal device. Further by detecting the transmitted portion of the incident light flux, an optical anisotropy of the object to be examined at a position other than a boundary thereof can be measured simultaneously.

14 Claims, 6 Drawing Sheets

FIG. 9

APPARATUS AND METHOD FOR MEASURING OPTICAL ANISOTROPY

FIELD OF THE INVENTION AND RELATED ART

The present invention relates to an apparatus and a method for measuring an optical anisotropy of a material. More particularly, the present invention relates to an apparatus and a method for measuring an optical anisotropy of a liquid crystal in order to determine a pretilt angle of the liquid crystal in a liquid crystal device.

An apparatus for measuring an optical anisotropy of a certain material have been used in various fields. Hereinbelow, explanation will be made based on determination of a pretilt angle in a liquid crystal device for example.

In production of a liquid crystal device, a treatment for aligning liquid crystal molecules, such as rubbing, has been generally performed. By the aligning treatment, liquid crystal molecules are aligned to form a certain angle (called a pretilt angle) with respect to a substrate surface in a liquid crystal device. An alignment state of liquid crystal in a liquid crystal device depends on a magnitude of the pretilt angle, and an alignment defect is liable to be caused by nonuniform pretilt angles. Accordingly, the measurement or determination of pretilt angle is indispensable for evaluation of a liquid crystal alignment state and also for evaluation of optical performance of a liquid crystal device. Further, the measurement of a pretilt angle is also important for clarifying a phenomenon of liquid crystal molecules being aligned by rubbing and for developing and manufacturing liquid crystal devices having a uniform pretilt angle and less defects.

Figure 1:
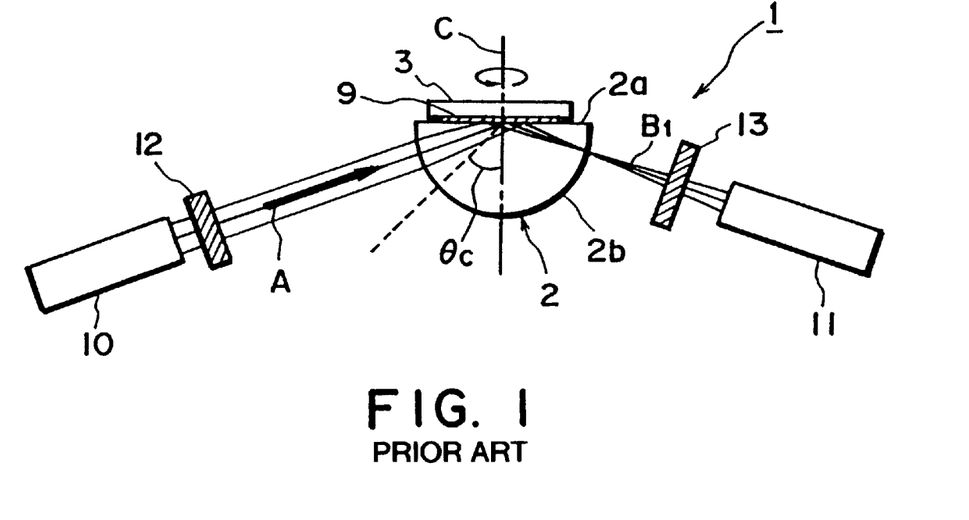
FIG. 1 illustrates a conventional optical anisotropy measurement apparatus.

Accordingly, some methods and apparatus for determining a pretilt angle in a liquid crystal device through measurement of liquid crystal optical anisotropy have been widely known. FIG. 1 shows an example of such apparatus for measurement of optical anisotropy. More specifically, FIG. 1 is an illustration of an apparatus for optical anisotropy measurement according to a total reflection method, which will be described hereinafter.

Thus, FIG. 1 is a schematic illustration of a total reflection-type optical anisotropy measurement apparatus. Referring to FIG. 1, an optical anisotropy measurement apparatus 1 includes a hemispherical glass member (hereinafter simply called a "hemispherical glass") 2 having a flat surface 2a and a spherical surface 2b. As shown in a greater detail in FIG. 2, a glass substrate 3 is disposed opposite to the flat surface 2a, and the glass substrate 3 and the flat surface 2a are surface-coated with a transparent electrode 5 and an alignment film 6. The glass substrate 3 and the flat surface 2a are applied to each other with a sealing member 7, and a liquid crystal 9 as an object to be examined is sandwiched therebetween.

The hemispherical glass 2 is supported rotatably about a rotation axis C perpendicular to its flat surface 2a.

On the other hand, on one side (a left side as shown) of the hemispherical glass 2, a He-Ne laser 10 is disposed to emit an incident light flux A so as to be incident to the liquid crystal 9. On the other side (a right side as shown) of the hemispherical glass 2, a photodetector 11 is disposed so as to detect a reflected light flux B1 totally reflected at a boundary with the liquid crystal 9.

Between the hemispherical glass 2 and the He-Ne laser 10, a polarizer 12 is disposed so as to linearly polarize the incident light flux A. Further, between the hemispherical glass 2 and the photodetector 11, an analyzer 13 having a polarization direction perpendicular to that of the polarizer 12 is disposed.

By using the above-mentioned optical anisotropy measurement apparatus, an optical anisotropy measurement (a pretilt angle determination) has been performed in the following manner.

An incident light flux A emitted from the He-Ne laser 10 is linearly polarized by the polarizer 12, then incident to the hemispherical glass 2 and totally reflected at the boundary with the liquid crystal 9. During the total reflection, an evanescent wave occurs, once enters into into the liquid crystal 9 and is then reflected. The evanescent wave is caused to have a polarization state which varies depending on the optical anisotropy of the liquid crystal molecules in the vicinity of the boundary.

The reflected light flux B1 emitted from the hemispherical glass is once converged and then passes through the analyzer 13, whereby only a polarized light component having a polarization direction perpendicular to that of the polarizer 12 is allowed to reach the photodetector 11.

When the hemispherical glass 2 is rotated about the rotation axis C, the director of liquid crystal molecules (which is a unit vector representing the orientation direction of liquid crystal molecules) in the liquid crystal layer 7 is changed relative to the electric field vector direction of the incident light flux A.

Figure 3:
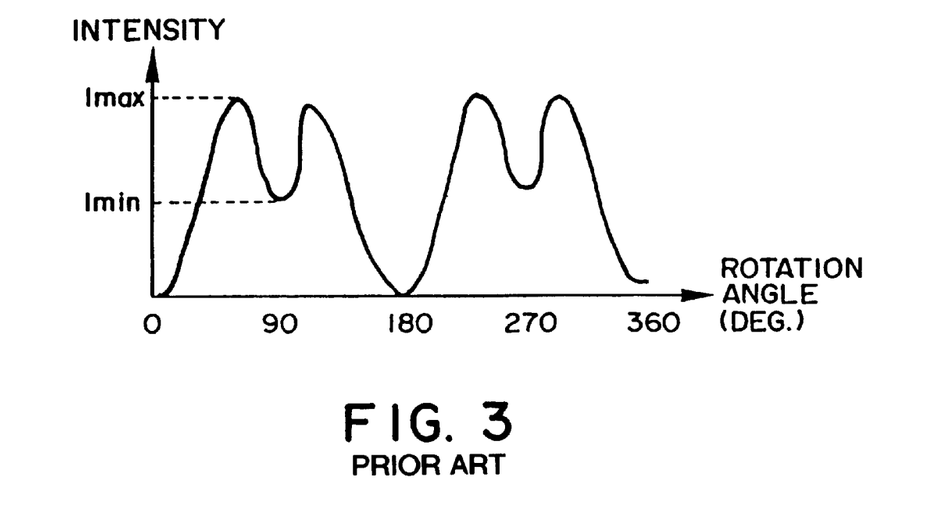
FIG. 3 is a graph showing an example of measured optical anisotropy pattern obtained by using such an optical anisotropy measurement apparatus.

As a result, corresponding to the rotation angle of the hemispherical glass 2, the polarization state of the reflected light flux B1 emitted from the hemispherical glass 2 is changed. By plotting the outputs of the photodetector 11 versus the rotation angles of the hemispherical glass 2, a characteristic curve, e.g., as shown in FIG. 3, representing the optical anisotropy of the liquid crystal is obtained. Now, if a maximum intensity and a minimum intensity on the curve are denoted by Imax and Imin, respectively, a pretilt angle can be determined from a ratio (Imax/Imin) therebetween. Incidentally, a larger pretilt angle corresponds to a smaller ratio Imax/Imin, and a smaller pretilt angle corresponds to a larger ratio Imax/Imin.

As described above, the optical anisotropy measurement apparatus 1 allows the measurement of the optical anisotropy of a liquid crystal based on a change in polarization state of the reflected light flux B1 corresponding to the interaction of the evanescent wave caused at the time of total reflection with liquid crystal molecules, and allows the determination of a pretilt angle based on the optical anisotropy.

Based on the property of the evanescent wave that it reaches only a narrow region from the boundary, the optical anisotropy of the liquid crystal in proximity to the boundary between the liquid crystal layer 9 and the alignment film 6 is measured.

Figure 4:
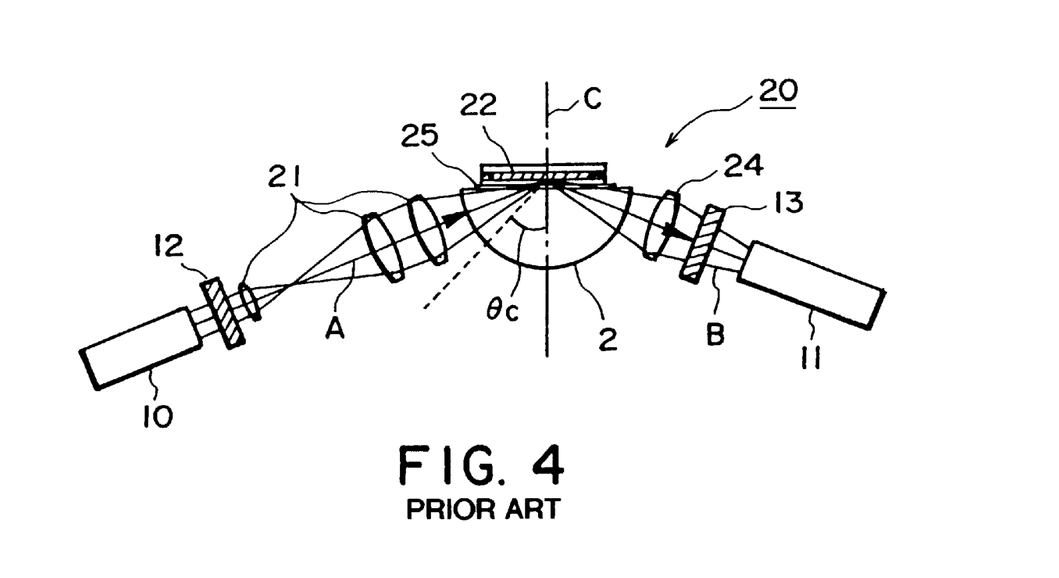
FIG. 4 illustrates our previously proposed optical anisotropy measurement apparatus.

On the other hand, FIG. 4 illustrates another optical anisotropy measurement apparatus which we have proposed previously (later published on Jul. 31, 1996 as European Laid-Open Application (EP-A) 0724147).

Referring to FIG. 4, an optical anisotropy measurement apparatus 20 includes an incident optical system 21 between a polarizer 20 and a hemispherical glass 2 so as to converge an incident light flux A. Further, an outgoing optical system 24 is disposed between the hemispherical glass 2 and an analyzer 13.

Incidentally, in the apparatus system shown in FIG. 4, a liquid crystal cell (device) 22 is disposed on a flat surface 2a of a hemispherical glass 2. As shown in an enlarged scale in FIG. 5, the liquid crystal cell 22 comprises a pair of glass substrates 23 each coated with a transparent electrode 5 and an alignment film 6 on its inner side. The substrates 23 are applied to each other with a sealing member 7 disposed at peripheral parts therebetween, and a liquid crystal 9 as an object to be examined is sandwiched therebetween. Further a refractive index-matching liquid 25 is disposed to fill a gap between the liquid crystal 22 and the hemispherical glass 2 so as to substantially equalize the refractive indexes of the liquid crystal cell 22, the hemispherical glass 2 and the refractive index-matching liquid 25.

In the above-described apparatus, the incident light flux A emitted from the incident optical system 21 is designed to be incident to the flat surface 2a and also the liquid crystal layer 9 wholly at an angle larger than the critical region diameter has amounted to ca. 8 μm.

For example, in case where the hemispherical glass has a refractive index of ca. 1.8 and the liquid crystal 9 has a refractive index of ca. 1.6, the critical angle becomes ca. 62.7 deg., and a light flux A is incident at an angle range of 62.7 deg. to 90 deg., by designing the incident optical system 21 to have an N.A. (numerical aperture) below 0.24. In this case, if the light flux A is assumed to have a wavelength of 632.8 nm, the light flux diameter becomes 1.8 μm at a minimum (actually 2 μm or larger because of aberration of the optical system). In this instance, as the light flux A is incident to the liquid crystal layer 9 at a large inclination in the above-mentioned total reflection method, the light flux illumination region at the boundary with the liquid crystal 9 becomes elliptical giving a longer axis of ca. 8 μm.

On the other hand, in an ordinary liquid crystal device used for display, one pixel has a size of several tens to several hundreds μm-square. Accordingly, in order to evaluate an alignment state for each pixel and also evaluate an alignment state of a spacing between pixels, the measurement region has to be reduced in size. Further, in order to evaluate an irregularity of alignment state within a single pixel, the measurement region is also required to be reduced in size. Particularly, not a few alignment defects have a size of 8 μm or smaller, so that the measurement region has to be inevitably reduced in size in order to detect such a minute alignment defect.

However, as the measurement apparatus 20 has required a measurement region size (longer diameter) of 8 μm or larger, it has been difficult to find such a minute alignment defect and compare the alignment state of the defective portion and another portion. As a result, it has been difficult to exactly detect the alignment state of the liquid crystal 9 and clarify the mechanism of defect occurrence.

On the other hand, the liquid crystal molecular alignment state can be frequently different between at a boundary with a substrate and at a bulk portion of the liquid crystal 9. However, according to a conventional measurement system, only the alignment state at a boundary with a substrate has been measured, so that it has been difficult to obtain sufficient information for clarifying a rubbing effect or optimizing drive voltages.

Further, the alignment state in a liquid crystal cell 22 is changed during its driven state, so that a pretilt angle measured only in a non-driven state cannot provide sufficient information.

SUMMARY OF THE INVENTION

Accordingly, an object of the present invention is to provide an apparatus and a method for optical anisotropy measurement allowing a measurement of a reduced size of measurement region.

Another object of the present invention is to provide an apparatus and a method for optical anisotropy measurement allowing a detection of a minute alignment defect in a liquid crystal device.

A further object of the present invention is to provide an apparatus and a method for optical anisotropy measurement effective for clarifying a mechanism of occurrence of alignment defects and developing a defect-free device.

A further object of the present invention is to provide an apparatus and a method for optical anisotropy measurement allowing measurement of an optical anisotropy not only of a boundary portion but also an internal or bulk portion of an object to be examined.

Another object of the present invention is to provide an apparatus and a method for optical anisotropy measurement allowing detection of alignment states at a boundary portion and a bulk portion of a liquid crystal.

A further object of the present invention is to provide an apparatus and a method for optical anisotropy measurement capable of changing the measurement position and reducing the size of measurement region.

A still further object of the present invention is to provide an apparatus and a method for optical anisotropy measurement allowing a measurement of alignment state of a liquid crystal during a drive.

According to the present invention, there is provided an optical anisotropy measurement apparatus, comprising:

an object to be examined with respect to its optical anisotropy, an object-holding means for holding the object to be examined, a light source for emitting a light flux toward the object to be examined, an incident optical system disposed between the light source and the object to be examined so as to converge the light flux from the light source, and a first photodetector for detecting a light flux totally reflected by the object to be examined, wherein the light source and the incident optical system are disposed so as to cause a portion of the light flux to be incident at an angle smaller than a critical angle to and transmitted through the object to be examined.

According to another aspect of the present invention, there is provided an optical anisotropy measurement method, comprising:

causing a light flux to be incident to an object to be examined via an incident optical system and detecting a light flux totally reflected from the object to be examined by a first photodetector to measure an optical anisotropy of the object to be examined, wherein the light source and the incident optical system are disposed so as to cause a portion of the light flux to be incident at an angle smaller than a critical angle to and transmitted through the object to be examined.

In the present invention, a light flux emitted from light source is totally reflected by the object to be examined to be detected by the first photodetector. However, a portion of the incident light flux is incident to the object to be examined at an angle smaller than a critical angle of total reflection and is allowed to be transmitted through the object to be examined, by appropriate disposition of the light source and the incident optical system. As a result, a light flux-incident region at the boundary causing the total reflection is allowed to have a shape closer to a circle and a smaller size, thus allowing detection of a local change in optical anisotropy.

These and other objects, features and advantages of the present invention will become more apparent upon a consideration of the following description of the preferred embodiments of the present invention taken in conjunction with the accompanying drawings, wherein like parts are denoted by like reference numerals.

DESCRIPTION OF THE PREFERRED EMBODIMENTS

Figure 6:
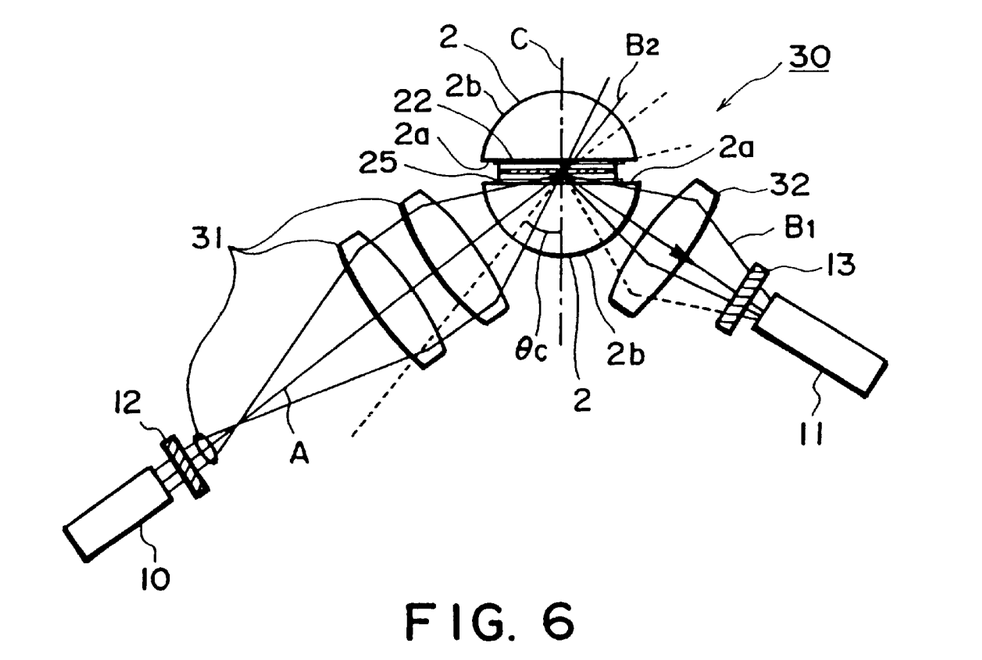
FIGS. 6, 8 and 9 are schematic illustrations of first, second and third embodiments, respectively, of the optical anisotropy measurement apparatus according to the invention.

A first embodiment of the present invention will now be described with reference to FIGS. 6 and FIG. 6 is a schematic illustration of a first embodiment of the optical anisotropy measurement apparatus according to the present invention.

Referring to FIG. 6, an optical anisotropy measurement apparatus 30 includes two hemispherical transparent glass members (hereinafter each called a "hemispherical glass") 2 as object-holding means. Each hemispherical glass 2 has a flat surface 2a and a spherical surface 2b, and two flat surfaces 2a of the pair of hemispherical glasses 2 are disposed opposite to each other with a prescribed spacing therebetween.

Figure 5:
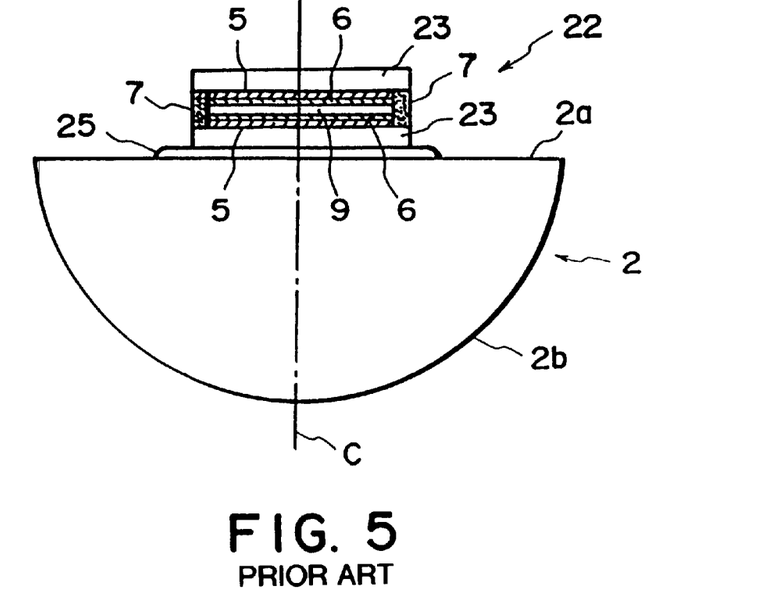
FIG. 5 is an enlarged view around a hemispherical glass in the apparatus shown in FIG. 4.
Figure 7:
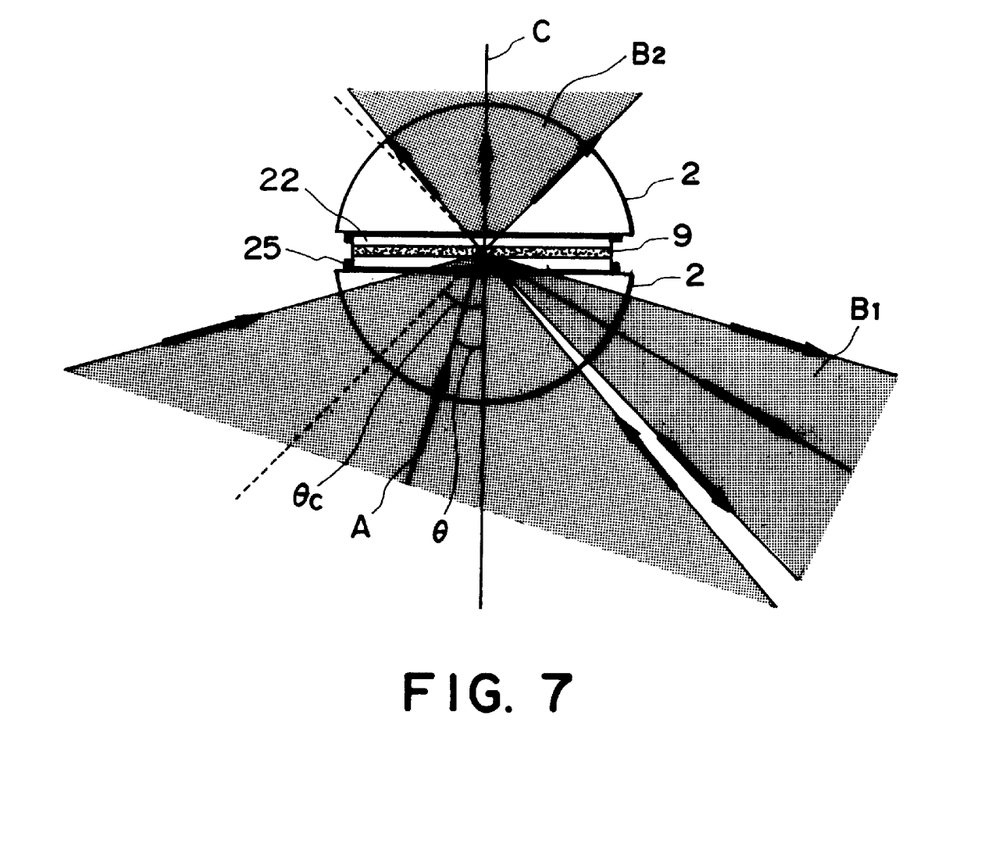
FIG. 7 is a schematic illustration of total reflection and transmission of an incident light flux.

Between the two hemispherical glass 2, a liquid crystal cell 2 as described with reference to FIG. 5 is held (also as shown in FIG. 7). The liquid crystal cell 22 comprises a pair of glass substrates 23, and a liquid crystal 9 (as an object to be examined) disposed between the substrates 23.

A gap between the liquid crystal cell 22 and each hemispherical glass 2 is filled with a refractive index-matching liquid 25, so that the substrates 23 of the liquid crystal cell 22, the hemispherical glasses 2 and the refractive index-matching liquid 25 will have identical refractive indexes. More specifically, it is preferred that the refractive index difference between the hemispherical glass 2 and the liquid 25, and the refractive index difference between the liquid 25 and the glass substrate 23, are respectively set to be within a range of ±0.05.

On one side of the hemispherical glass 2, a He-Ne laser (light source) 2 and a polarizer 12 are disposed and, between the polarizer 12 an the hemispherical glass 2, an incident optical system 31 is disposed. The He-Ne laser 10, the polarizer 12 and the incident optical system 31 are so disposed that a portion of the light flux A is incident at an angle smaller than a critical angle θc of total reflection to provide a transmitted light flux B2 transmitted through the liquid crystal 9.

In this embodiment, the incident optical system 31 is designed to have an N.A. (numerical aperture) satisfying the following relationship with the critical angle θc (deg.):

$$N.A. \leq \sin[(90+\theta c)/2] \qquad (1).$$

More specifically, N.A. may appropriately be set to at most 0.94 (corresponding to θc=50 deg. in the above formula).

On the other hand, on the opposite side with respect to the hemispherical glass 2, an outgoing optical system 32, an analyzer 13 and a photodetector (first detector) 11 are disposed, so that a reflected light flux B1 totally reflected at a boundary with the liquid crystal is detected by the photodetector 11 for measuring the optical anisotropy, from which an alignment state of the liquid crystal at the boundary is evaluated.

The reason for setting the N.A. of the incident optical system 31 to be at most 0.94 is as follows.

The light flux A incident to the liquid crystal boundary is required to include a portion thereof (reflected light flux B1) totally reflected toward the side the photodetector 11 (lower right side in FIGS. 6 and 7), and another portion (light flux B2) is transmitted through the liquid crystal 9 and need not be totally reflected. For this purpose, it is preferred that the incident light flux A comprises a bundle of light rays having incident angles θ (deg.) (taken as "positive in a clockwise (leftward) direction and "negative" in a counterclockwise (rightward) direction with respect to a rotation axis C in FIGS. 6 and 7) within a range of −θc≦θ≦90. Now, if the critical angle of total reflection is taken as 50 deg. (corresponding to case, for example, including a liquid crystal having a refractive index of 1.5 and a glass having a refractive index of 1.9), it is preferred that the N.A. of the incident optical system 31 is designed to be 0.94 (=sin[(90+50)/2]) at the maximum.

The hemispherical glass 2 may preferably have a shape of a hemisphere or a shape close thereto, and a curvature center in the measurement region or a region close thereto. The hemispherical glass 2 and the glass substrate 23 (FIG. 5) of the liquid crystal cell 2 may preferably comprise a high refractive index glass having a refractive index of at least 1.7, more preferably at least 1.75, of, e.g., heavy flint glass. It is possible to alternatively use a transparent material free from optical anisotropy other than glass. It is preferred to use a material having a refractive index larger than that of a liquid crystal 9 as an object to be examined.

The light source 10 can be an Ar laser, a semiconductor laser or a beam or light flux emission apparatus other than a laser, such as a thermal radiation source, in addition to the He-Ne laser but may preferably comprise an apparatus emitting a beam or light flux that can be condensed. The light source 10, such as a He-Ne laser, may preferably be one free from aberration such as astigmatism and capable of emitting a monochromatic light flux A free from chromatic aberration. The photodetector 11 may comprise an optical power meter, a photomultiplier, etc., but may preferably be one having a broad dynamic range.

Now, an optical anisotropy measurement method (method of determining a pretilt angle) by using the optical anisotropy measurement apparatus 30 will be described.

In this embodiment, a light flux A emitted from the He-Ne laser 10 is linearly polarized by passing through the polarizer 12 and converged by passing through the incident optical system 31 and enters into the hemispherical glass 2 from the spherical surface 2b.

Then, a portion (light flux B1) of the incident light flux A enters the liquid crystal boundary at an angle larger than the critical angle θc to be totally reflected at the boundary. Then, during the total reflection, an evanescent wave occurs and once penetrates into the liquid crystal to be reflected while its polarization state is changed by liquid crystal molecules. The resultant reflected light flux B1 is emitted out of the spherical surface 2b of the hemispherical glass 2, and then passes through the outgoing optical system 32 and the analyzer 13 to be detected by the photodetector.

Figure 2:
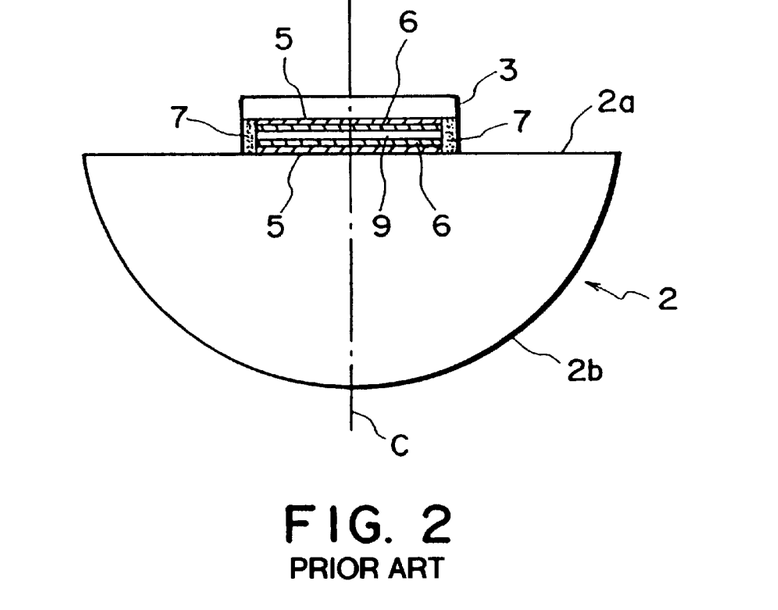
FIG. 2 is an enlarged view around a hemispherical glass in the apparatus shown in FIG. 1.

By performing the above-mentioned measurement while rotating the hemispherical glass 2 about its rotation axis C, a pretilt angle at the liquid crystal boundary may be determined. More specifically, by using a ratio Imax/Imin of a resultant intensity vs. rotation angle characteristic curve as shown in FIG. 2 and boundary conditions for total reflection, Maxwell's equations may be solved to determine a pretilt angle (Jiuzhi Xue, et al, Appl. Phys. Lett. 53 (1988) 2397–2399; H. P. Hinov, et al., Revue Phys. Appl. 15 (1980) 1307–1321; etc.)

On the other hand, as another portion of the incident light flux A is incident to boundary of the liquid crystal 9, a portion thereof is allowed to be transmitted through the liquid crystal cell 22 without total reflection to provide a transmitted light flux B2, and the remaining portion is emitted at the boundary as ordinary reflected light. Unlike the evanescent wave caused by the total reflection, the ordinary reflected light has not caused a change in polarization state and is therefore not allowed to be transmitted through the analyzer 13 to be detected by the photodetector 11. As the upper side of the liquid crystal cell 22 is covered with an upper hemispherical glass 2 with a refractive index-matching liquid 25 disposed therebetween, the transmitted light flux B2 is not totally reflected at boundaries with these member or detected by the photodetector 11 accordingly.

The effects of this embodiment will now be described.

In this embodiment, a portion of the light flux A is designed to be incident at an angle smaller than the critical angle θc, so that the light flux-illuminating region is caused to have a shape which approaches a circle from an ellipse as in a conventional system. As a result, the light flux A incident to the liquid crystal 9 can be further converged (as to possibly provide a light flux diameter of 2 μm or smaller), and the measurement region can be reduced in size.

Further, if the incident optical system 31 is designed to have a large numerical aperture N.A. within the range governed by the formula (1), e.g., 0.94 or smaller for θc=50 deg., the measurement region size is reduced.

In a specific case wherein the light flux A has a wavelength of 632.8 nm, the incident optical system has an N.A. of ca. 0.43 and the light flux A is incident at an angle of ca. 63 deg., the light flux diameter may be ca. 1 μm and the measurement region diameter may be ca. 2.2 μm. Further, in case where the incident angle is reduced to ca. 48 deg. with the same light flux and incident optical system, the measurement region diameter can be reduced down to ca. 1.5 μm. If the wavelength of the incident light flux A is shorter than 632.8 nm, the measurement region diameter can be further reduced.

Thus, in this embodiment, as the measurement region diameter can be decreased, the alignment state (or ununiformity of alignment state) of a liquid crystal can be accurately measured, thus allowing detection of a minute alignment defect. The apparatus 30 is also effective in clarifying the mechanism of occurrence of alignment defect and developing a defect-free device.

The optical anisotropy measurement apparatus 30 is effective for examining not only an active matrix-type liquid crystal device but also a simple matrix-type liquid crystal device to detect an alignment irregularity, provide useful information for improving the alignment step and uniformize the product quality by detecting an inferior product.

Further, in this embodiment, a portion of the incident light flux A is allowed to be transmitted through the liquid crystal 9 to form a transmitted light flux B2 but, as the upper side of the liquid crystal cell 22 is coated with an upper hemispherical glass 2 via a refractive index-matching liquid 25, the transmitted light flux B2 is prevented from being totally reflected at boundaries with these members to provide a light fraction detectable by and deteriorating the measurement accuracy of the photodetector 11.

In the above-described embodiment, the upper hemispherical glass 2 disposed on the liquid crystal cell 22 can be replaced by a prism or an array of prisms.

Next, a second embodiment of the present invention will be described with reference to FIG. 8.

Figure 8:
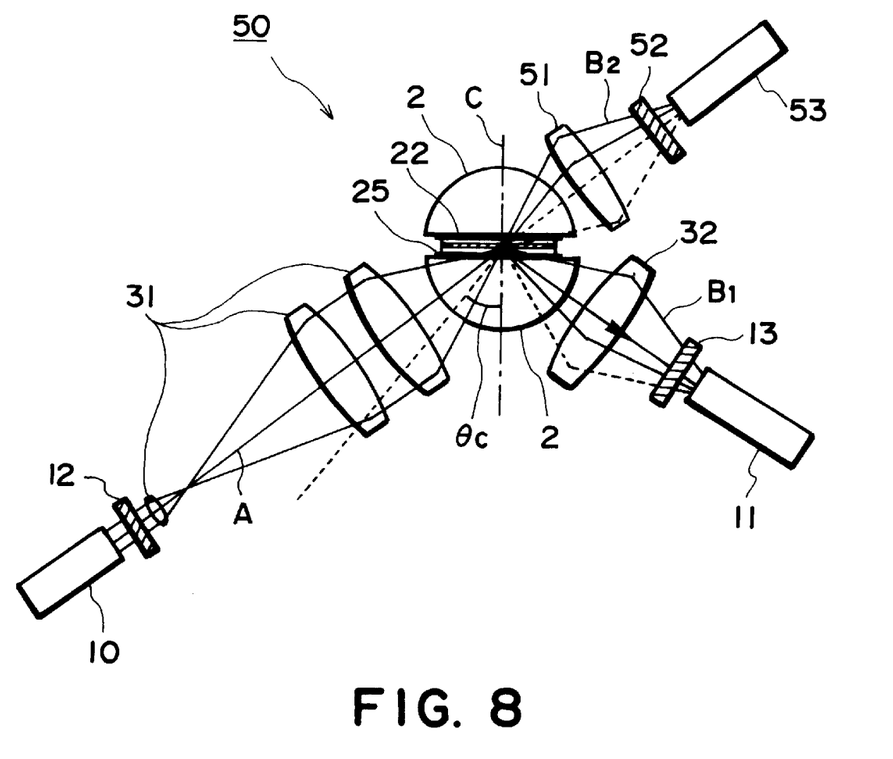

Referring to FIG. 8, in an optical anisotropy measurement apparatus 50 according to this embodiment, in the light path of a light flux B2 transmitted through an upper hemispherical glass 2, an outgoing optical system 51, an analyzer 52 and a photodetector (second photodetector) 53 are disposed, so that the transmitted light flux B2 can be detected by the photodetector 53.

The other members and organization of the apparatus 50 are identical to those in the apparatus 30 of the first embodiment.

Optical anisotropy measurement (or pretilt angle determination) may be performed by using the apparatus 50 of this embodiment in the following manner.

An He-Ne laser 10 is operated to emit a measurement light flux A, which is then linearly polarized by a polarizer 12 converged by an incident optical system 31 and transmitted through a lower hemispherical glass 2 to illuminate a liquid crystal 9.

As a result, a portion of the incident light flux A is totally reflected at the liquid crystal boundary and transmitted through an outgoing optical system 32 and an analyzer 13 to be detected by a photodetector (first photodetector) 11, whereby the optical anisotropy of the liquid crystal is measured and, based thereon, a pretilt angle is determined at the liquid crystal boundary.

On the other hand, another potion of the light flux A is incident to the liquid crystal 9 at an angle smaller than the critical angle θc to be transmitted through the liquid crystal to provide a transmitted light flux B2, which is then detected by the second detector 53 disposed in the light path of the transmitted light flux B2. Based on the detection result, an alignment state in the bulk phase can be evaluated.

According to this embodiment, an intensity change of reflected light flux B1 from the liquid crystal boundary is detected by the first photodetector 11 while rotating the optical system about the rotation axis C to evaluate the alignment state at the liquid crystal boundary, and an intensity change of transmitted light flux B2 is detected by the second photodetector 53 to evaluate the alignment state or contrast or transmittance change in the bulk portion in connection with the alignment state at the boundary. Further, by evaluating the differences in these alignment states, it becomes possible to clarify he effect of rubbing step and obtain useful information for optimizing drive voltages.

Also in this embodiment, similarly as in the above-mentioned first embodiment, a portion of the light flux A is caused to be incident at an angle smaller than the critical angle θc the light flux-illuminating region at the liquid crystal boundary is caused to have a shape closer to a circle, so that the measurement region diameter can be reduced in size correspondingly.

Further, if the N.A. of the incident optical system 31 is enlarged within the range of at most 0.94, the light flux A incident to the liquid crystal 9 can be further converged, thereby further reducing the measurement region size.

In the above-mentioned first and second embodiments, the hemispherical glass 2 and the liquid crystal cell 22 are provided as separated bodies but can be composed integrally in a structure as shown in FIG. 2. More specifically, a liquid crystal 9 as an object to be examined can be sandwiched between a hemispherical glass 2 as an object-holding means and a glass substrate 3. Further, it is also possible to sandwich the liquid crystal 9 between a pair of hemispherical glasses 2 without using a glass substrate 3.

Next, a third embodiment of the present invention will be described with reference to FIG. 9.

Figure 9:
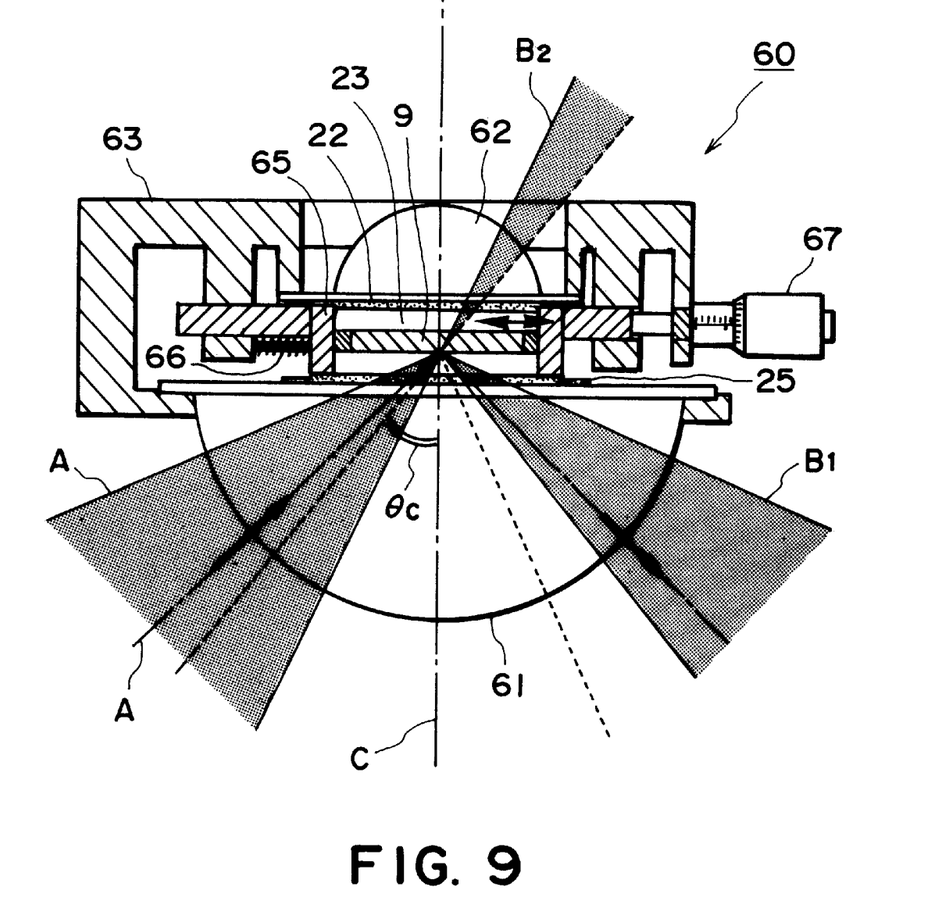

Referring to FIG. 9, an optical anisotropy measurement apparatus 60 is provided with two hemispherical glasses including a lower hemispherical glass 61 and an upper hemispherical glass 62 which is smaller in size than the lower hemispherical glass 61.

Of these, the lower hemispherical glass 61 is provided with a hemispherical glass-holder 63 affixed thereto, and the hemispherical glass-holder 63 is extended up to a position above the lower hemispherical glass 61 so as to hold the upper hemispherical glass 62 at a prescribed position. Further, the hemispherical glass-holder 63 also supports a liquid crystal cell-holder 65 movably relative to the upper and lower hemispherical glasses 61 and 62, and the cell-holder 65 is pressed rightwards by means of a coil spring 66 also affixed to the hemispherical glass-holder 63. Further, a micrometer 67 is also affixed to the hemispherical glass-holder 63 so as to place the liquid crystal cell 22 at an accurate position. Incidentally, the coil spring 66 and the micrometer 67 may be disposed in a single pair as shown in FIG. 9, but an additional pair of these members can be disposed in a direction perpendicular to the drawing, so as to measure the position of the liquid crystal cell 22 two-dimensionally.

Further, a refractive index-matching liquid 25 is disposed between the liquid crystal cell 22 and each of the hemispherical glasses 61 and 62 so as to allow a smooth movement of the liquid crystal cell 22.

Further, it is also possible to use a drive mechanism (not shown) for moving the liquid crystal cell-holder 65 at a high accuracy.

The hemispherical glass-holder 63 is equipped with a rotatively driving mechanism (not shown) so as to rotate the hemispherical glass 61, etc., about the rotation axis C relative to the optical system.

This embodiment can exhibit the following effects.

According to this embodiment, the liquid crystal cell 22 can be moved along the flat surfaces of the hemispherical glasses 61 and 62 to easily change the measurement position. As a result, it becomes easy to detect an alignment irregularity and the presence or absence of alignment defects. In this instance, the use of the micrometer allows a confirmation of an accurate measurement position and thus an accurate measurement of an alignment irregularity, etc.

Also in this embodiment, similarly as in the above-mentioned first embodiment, a portion of the light flux A is caused to be incident at an angle smaller than the critical angle θc and the light flux-illuminating region at the liquid crystal boundary is caused to have a shape closer to a circle, so that the measurement region diameter can be reduced in size correspondingly.

Further, if the N.A. of the incident optical system 31 is enlarged within the range of at most 0.94, the light flux A incident to the liquid crystal 9 can be further converged, thereby further reducing the measurement region size.

Further, by disposing a second photodetector (not shown) for detecting a transmitted light flux B2, it becomes possible to evaluate the alignment state of a bulk portion of the liquid crystal 9 similarly as in the second embodiment.

According to a fourth embodiment of the present invention, by using an optical anisotropy measurement apparatus as shown in FIG. 6, 8 or 9 described above, the optical anisotropy of the liquid crystal 9 in the liquid crystal cell 22 may be subjected optical anisotropy measurement while it is driven under application of voltages. Herein, the driven state of a liquid crystal means a state of the liquid crystal changing its transmittance or scattering state with time.

More specifically, by using an optical anisotropy measurement apparatus as shown in FIG. 6, for example, an alignment state in a minute region under drive can be measured.

Further, by using an optical anisotropy measurement apparatus as shown in FIG. 8 including a second photodetector 53 and an associated optical system for detecting a transmitted light flux B2, it is possible to evaluate the alignment state or contrast change in a bulk portion under drive in connection with the alignment state at the boundary.

Further, if an optical anisotropy measurement apparatus 60 as shown in FIG. 9 is included, the measurement region can be easily changed.

The liquid crystal 9 in the liquid crystal cell 22 can also be driven or changed by applying an external energy, such as heat or magnetic field, instead of applying an electric field as in the present embodiment.

As described hereinabove, according to the present invention, a portion of incident light flux is caused to be incident to an object to be examined at an angle smaller than a critical angle and allowed to be transmitted through the object to be examined by arranging the light source and the incident optical system, whereby a distortion of the incident light flux-illuminating region is alleviated to provide a shape closer to a circle of illuminated region, thus allowing a reduced size (longer axis) of measurement region. This effect is further pronounced, if the incident optical system is designed to have a numerical aperture N.A. within a range of satisfying the following relationship with the critical angle θc:

$$N.A. \leq \sin[(90+\theta c)/2].$$

Now, in the case where a liquid crystal is used as-an object to be examined and disposed between a pair of glass substrates to constitute a liquid crystal cell, and the liquid crystal cell is held on an object-holding means via a refractive index-matching liquid having a refractive index substantially identical to those of the glass substrate and the object-holding means, the liquid crystal alignment state at the boundary can be detected by the first photodetector so as to allow the detection of a minute alignment defect and an accurate detection of a liquid crystal alignment state. Further, it is possible to obtain information useful for clarifying the occurrence of alignment defect and for developing a defect-free device. In this instance, the object-holding means can be disposed in a pair so as to sandwich the liquid crystal cell therebetween. A similar effect can be attached also in the case where the liquid crystal as an object to be examined is sandwiched between the object-holding means and a glass substrate.

On the other hand, in the case where a second photodetector is disposed so as to detect a light flux transmitted through the object to be examined in combination with the first photodetector for detecting the reflected light flux, the optical anisotropy of the object to be examined can be examined in various aspects including those at the boundary and at the bulk portion.

Herein, in case of using a liquid crystal as an object to be examined disposed between a pair of glass substrates to form a liquid crystal cell, the liquid crystal alignment state at the boundary can be detected by the first photodetector and the liquid crystal alignment state at a bulk portion can be detected by the second photodetector. Further, by evaluating the differences of these alignment states, it is possible to obtain information effective for clarifying the performance of a rubbing step and for optimizing drive voltages. In this instance, the object-holding means can be disposed in a pair so as to sandwich the liquid crystal cell therebetween. A similar effect can be attained also in the case where the liquid crystal as an object to be examined is sandwiched between the object-holding means and a glass substrate.

Further, if a liquid crystal cell constituted thereabove is disposed on an object-holding means via a refractive index-matching liquid so as to be movable relative to the object-holding means, the measurement position in the liquid crystal can be changed so as to allow an easy comparison of an alignment state or a liquid crystal molecular switching characteristic between an alignment defect portion and an alignment defect-free portion.

If the above-described measurement is performed with respect to a liquid crystal under drive, the alignment state of the liquid crystal in the driven state can be evaluated.

What is claimed is:

1. An optical anisotropy measurement apparatus, comprising:
   an object to be examined with respect to its optical anisotropy,
   an object-holding means for holding the object to be examined,
   a light source for emitting a light flux toward the object to be examined,
   an incident optical system disposed between the light source and the object to be examined so as to converge the light flux from the light source, and
   a first photodetector for detecting a light flux totally reflected by the object to be examined,
   wherein the light source and the incident optical system are disposed so as to provide a convergent light flux and cause a portion of the light flux to be incident at an angle smaller than a critical angle to and transmitted through the object to be examined.

2. An apparatus according to claim 1, wherein said incident optical system is designed to have a numerical aperture N.A. satisfying the following relationship with the critical angle denoted by θc (deg.):
   N.A.≦sin [(90+θc)/2].

3. An apparatus according to claim 1, wherein the N.A. of the incident optical system is at most 0.94.

4. An apparatus according to claim 1, further including a second photodetector disposed so as to detect a light flux transmitted through the object to be examined, whereby the optical anisotropy of the object to be examined is detected by the first and second photodetectors.

5. An apparatus according to claim 1, wherein said object to be examined comprises a liquid crystal disposed between the object-holding means and a glass substrate so as to allow detection of an alignment state of the liquid crystal.

6. An apparatus according to claim 1, wherein said object to be examined comprises a liquid crystal disposed between a glass substrates so as to form a liquid crystal cell, the liquid crystal cell is held by the object-holding means; a refractive index-matching liquid is disposed to fill a gap between the liquid crystal cell and the object-holding means, and the glass substrates, the object-holding means and the refractive index-matching liquid are designed to have substantially identical indexes so as to allow detection of an alignment state of the liquid crystal.

7. An apparatus according to claim 6, wherein the object-holding means are disposed in a pair, and the liquid crystal cell is held in a sandwiched form between the pair of the object-holding means.

8. An apparatus according to claim 6, wherein said liquid crystal cell is disposed movably relative to the object-holding means, so as to allow a change of measurement position.

9. An apparatus according to claim 5, wherein said liquid crystal is disposed so as to allow detection of alignment state in its driven state.

10. An apparatus according to claim 1, wherein said object-holding means comprises a hemispherical glass member having a spherical surface and a flat surface, and the light flux from the light source is transmitted through the object-holding means to be incident to the object to be examined.

11. An optical anisotropy measurement method, comprising:
    causing a light flux to be incident to an object to be examined via an incident optical system; and
    detecting a light flux totally reflected from the object to be examined by a first photodetector to measure an optical anisotropy of the object to be examined,
    wherein the light source and the incident optical system are disposed so as to provide a convergent light flux and cause apportion of the light flux to be incident at an angle smaller than a critical angle to and transmitted through the object to be examined.

12. A method according to claim 11, wherein said portion of the light flux transmitted through the object to be examined is detected by a second photodetector.

13. A method according to claim 11, wherein said object to be examined comprises a liquid crystal disposed between a glass substrates so as to form a liquid crystal cell, the liquid crystal cell is held by the object-holding means; a refractive index-matching liquid having a refractive index substantially identical to those of the glass substrates and the object-holding means is disposed to fill a gap between the liquid crystal cell and the object-holding means, and the liquid crystal cell is moved relative to the object-holding means so as to allow measurement of an alignment state of the liquid crystal at varying positions.

14. A method according to claim 13, wherein the liquid crystal is subjected to measurement of an alignment state in its driven state.

* * * * *

UNITED STATES PATENT AND TRADEMARK OFFICE
CERTIFICATE OF CORRECTION

PATENT NO. : 6,088,115
DATED : July 11, 2000
INVENTOR(S) : Yoshinori Ohsaki et al.

It is certified that error appears in the above-identified patent and that said Letters Patent is hereby corrected as shown below:

Title page,
Item [56], References Cited, OTHER PUBLICATIONS, after "Takezoe, H. et al.", "Calls:" should read -- Cells: --.

Column 1,
Line 14, "have" should read -- has --;
Line 33, "less" should read -- fewer --; and
Line 47, "in a" should read -- in --.

Column 2,
Line 12, "into into the" should read -- into the --.

Column 3,
Line 17, "has amounted" should read -- amounts --; and
Line 52, "between" should be deleted.

Column 4,
Line 60, "emitted from" should read -- emitted from the --.

Column 5,
Line 34, "6 and" should read -- 6 and 7 --;
Line 46, "glass 2," should read -- glasses 2, --;
Line 47, "cell 2" should read -- cell 22 --;
Line 62, "(light source) 2" should read -- (light source) 10 --; and
Line 63, "12 an" should read -- 12 and --.

Column 6,
Line 24, "the side the" should read -- the side of --;
Line 34, "to case" should read -- to a case --; and
Line 43, "liquid crystal cell 2" should read -- liquid crystal cell 22 --.

Column 7,
Line 35, "member" should read -- members --; and
Line 54, "case" should read -- a case --.

Column 8,
Line 61, "he effect of rubbing" should read -- the effect of the rubbing --; and
Line 66, "angle θc the" should read -- angle θc, and the --.

UNITED STATES PATENT AND TRADEMARK OFFICE
CERTIFICATE OF CORRECTION

PATENT NO.   : 6,088,115
DATED        : July 11, 2000
INVENTOR(S)  : Yoshinori Ohsaki et al.

It is certified that error appears in the above-identified patent and that said Letters Patent is hereby corrected as shown below:

Column 10,
Line 13, "subjected" should read -- subjected to --; and
Line 66, "attached" should read -- attained --.

Column 12,
Line 7, "a glass" should read -- glass --;
Line 24, "of alignment" should read -- of the alignment --;
Line 41, "apportion" should read -- a portion --; and
Line 51, "a glass" should read -- glass --.

Signed and Sealed this

Thirtieth Day of July, 2002

Attest:

JAMES E. ROGAN
Attesting Officer    Director of the United States Patent and Trademark Office